(12) United States Patent
Zubok et al.

(10) Patent No.: US 7,468,076 B2
(45) Date of Patent: Dec. 23, 2008

(54) ARTIFICIAL INTERVERTEBRAL DISC HAVING A UNIVERSAL JOINT

(75) Inventors: Rafail Zubok, Midland Park, NJ (US); Michael W. Dudasik, Nutley, NJ (US); Joseph P. Errico, Green Brook, NJ (US)

(73) Assignee: SpineCore, Inc., Summit, NJ (US)

( * ) Notice: Subject to any disclaimer, the term of this patent is extended or adjusted under 35 U.S.C. 154(b) by 28 days.

(21) Appl. No.: 11/062,008

(22) Filed: Feb. 18, 2005

(65) Prior Publication Data

US 2005/0246022 A1 Nov. 3, 2005

Related U.S. Application Data

(60) Provisional application No. 60/546,230, filed on Feb. 20, 2004.

(51) Int. Cl.
*A61F 2/44* (2006.01)
(52) U.S. Cl. ............. 623/17.11; 623/16.11; 623/17.14
(58) Field of Classification Search .... 623/17.11–17.16
See application file for complete search history.

(56) References Cited

U.S. PATENT DOCUMENTS

| | | | |
|---|---|---|---|
| 2,193,122 A | 3/1940 | Crabbs | |
| 3,867,728 A | 2/1975 | Stubstad et al. | |
| 4,309,777 A | 1/1982 | Patil | |
| 4,566,466 A | 1/1986 | Ripple et al. | |
| 4,605,417 A | 8/1986 | Fleischauer | |
| 4,759,766 A * | 7/1988 | Buettner-Janz et al. | 623/17.15 |
| 4,759,769 A * | 7/1988 | Hedman et al. | 623/17.13 |
| 4,932,969 A | 6/1990 | Frey et al. | |
| 4,997,432 A | 3/1991 | Keller | |
| 5,034,254 A | 7/1991 | Cologna et al. | |
| 5,236,460 A | 8/1993 | Barber | |
| 5,258,031 A * | 11/1993 | Salib et al. | 623/17.15 |
| 5,306,308 A * | 4/1994 | Gross et al. | 623/17.16 |
| 5,314,477 A * | 5/1994 | Marnay | 623/17.15 |
| 5,370,697 A | 12/1994 | Baumgartner | |
| 5,401,269 A * | 3/1995 | Buttner-Janz et al. | 623/17.15 |
| 5,425,773 A * | 6/1995 | Boyd et al. | 623/17.15 |
| 5,507,816 A * | 4/1996 | Bullivant | 623/17.15 |
| 5,556,431 A * | 9/1996 | Buttner-Janz | 623/17.15 |
| 5,562,738 A * | 10/1996 | Boyd et al. | 623/17.15 |
| 5,674,296 A * | 10/1997 | Bryan et al. | 623/17.16 |
| 5,676,701 A * | 10/1997 | Yuan et al. | 623/17.15 |
| 5,676,702 A | 10/1997 | Ratron | |
| 5,683,464 A | 11/1997 | Wagner et al. | |
| 5,683,465 A | 11/1997 | Shinn et al. | |

(Continued)

FOREIGN PATENT DOCUMENTS

WO WO-97/10776 A2 3/1997

*Primary Examiner*—David Isabella
*Assistant Examiner*—Ann Schillinger
(74) *Attorney, Agent, or Firm*—Lerner, David, Littenberg, Krumholz & Mentlik, LLP

(57) ABSTRACT

An artificial intervertebral implant including a first baseplate having a top surface, a bottom surface, an aperture extending therethrough and a strap attached to the bottom surface of the first baseplate and underlying the aperture. The implant further includes a second baseplate juxtaposed with the first baseplate. The second baseplate includes a top surface with a cavity exposed therein. An articulating element is attached to a pair of opposing sidewalls of the cavity for retaining the strap within the cavity.

14 Claims, 7 Drawing Sheets

U.S. PATENT DOCUMENTS

| | | |
|---|---|---|
| 5,755,796 A | 5/1998 | Ibo et al. |
| 5,782,830 A | 7/1998 | Farris |
| 5,782,832 A * | 7/1998 | Larsen et al. ............... 606/61 |
| 5,827,328 A | 10/1998 | Butterman |
| 5,865,846 A | 2/1999 | Bryan et al. |
| 5,888,226 A * | 3/1999 | Rogozinski ............. 623/17.16 |
| 5,893,889 A | 4/1999 | Harrington |
| 5,895,428 A * | 4/1999 | Berry ..................... 623/17.15 |
| 5,899,941 A * | 5/1999 | Nishijima et al. ......... 623/17.15 |
| 5,989,291 A | 11/1999 | Ralph et al. |
| 6,001,030 A | 12/1999 | Bryan et al. |
| 6,019,792 A * | 2/2000 | Cauthen ................. 623/17.14 |
| 6,039,763 A | 3/2000 | Shelokov |
| 6,063,121 A * | 5/2000 | Xavier et al. ............. 623/17.15 |
| 6,066,174 A | 5/2000 | Farris |
| 6,113,637 A | 9/2000 | Gill et al. |
| 6,136,031 A | 10/2000 | Middleton |
| 6,146,421 A * | 11/2000 | Gordon et al. ............ 623/17.15 |
| 6,156,067 A | 12/2000 | Bryan et al. |
| 6,159,215 A | 12/2000 | Urbahns et al. |
| 6,179,874 B1 | 1/2001 | Cauthen |
| 6,228,118 B1 | 5/2001 | Gordon |
| 6,280,458 B1 | 8/2001 | Boche et al. |
| 6,319,257 B1 | 11/2001 | Carignan et al. |
| 6,368,350 B1 | 4/2002 | Erickson et al. |
| 6,375,682 B1 | 4/2002 | Fleischmann et al. |
| 6,416,551 B1 | 7/2002 | Keller |
| 6,428,544 B1 | 8/2002 | Ralph et al. |
| 6,436,102 B1 | 8/2002 | Ralph et al. |
| 6,471,725 B1 | 10/2002 | Ralph et al. |
| 6,478,796 B2 | 11/2002 | Zucherman et al. |
| 6,478,800 B1 | 11/2002 | Fraser et al. |
| 6,478,801 B1 | 11/2002 | Ralph et al. |
| 6,517,580 B1 | 2/2003 | Ramadan et al. |
| 6,527,804 B1 | 3/2003 | Gauchet et al. |
| 6,554,864 B2 | 4/2003 | Ralph et al. |
| 6,562,047 B2 | 5/2003 | Ralph et al. |
| 6,579,320 B1 | 6/2003 | Gauchet et al. |
| 6,582,466 B1 * | 6/2003 | Gauchet .................. 623/17.11 |
| 6,582,468 B1 | 6/2003 | Gauchet |
| 6,592,624 B1 | 7/2003 | Fraser et al. |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,249 B2 | 11/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 * | 1/2004 | Viart et al. ............... 623/17.14 |
| 6,692,495 B1 | 2/2004 | Zacouto |
| 6,706,068 B2 | 3/2004 | Ferree |
| 6,716,245 B2 | 4/2004 | Pasquet et al. |
| 2001/0007073 A1 | 7/2001 | Zucherman et al. |
| 2001/0016773 A1 | 8/2001 | Serhan et al. |
| 2001/0020170 A1 | 9/2001 | Zucherman et al. |
| 2001/0039452 A1 | 11/2001 | Zucherman et al. |
| 2002/0062131 A1 | 5/2002 | Gallo, Sr. |
| 2002/0082695 A1 | 6/2002 | Neumann |
| 2002/0099377 A1 | 7/2002 | Zucherman et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111684 A1* | 8/2002 | Ralph et al. ............. 623/17.13 |
| 2002/0111685 A1 | 8/2002 | Ralph et al. |
| 2002/0128714 A1 | 9/2002 | Manasas et al. |
| 2002/0161375 A1 | 10/2002 | Ralph et al. |
| 2003/0014057 A1 | 1/2003 | Ralph et al. |
| 2003/0014109 A1 | 1/2003 | Ralph et al. |
| 2003/0014110 A1 | 1/2003 | Ralph et al. |
| 2003/0014112 A1 | 1/2003 | Ralph et al. |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023245 A1 | 1/2003 | Ralph et al. |
| 2003/0023309 A1 | 1/2003 | Ralph et al. |
| 2003/0023310 A1 | 1/2003 | Ralph et al. |
| 2003/0028197 A1 | 2/2003 | Hanson et al. |
| 2003/0028249 A1 | 2/2003 | Baccelli et al. |
| 2003/0028252 A1 | 2/2003 | Ralph et al. |
| 2003/0040801 A1 | 2/2003 | Ralph et al. |
| 2003/0040802 A1* | 2/2003 | Errico et al. ............. 623/17.14 |
| 2003/0055503 A1 | 3/2003 | O'Neil |
| 2003/0060886 A1 | 3/2003 | Van Hoeck et al. |
| 2003/0069586 A1 | 4/2003 | Errico et al. |
| 2003/0069642 A1 | 4/2003 | Ralph et al. |
| 2003/0074067 A1* | 4/2003 | Errico er al. ............. 623/17.14 |
| 2003/0100951 A1 | 5/2003 | Serhan et al. |
| 2003/0125748 A1 | 7/2003 | Li et al. |
| 2003/0149438 A1 | 8/2003 | Nichols et al. |
| 2003/0149482 A1 | 8/2003 | Michelson |
| 2003/0187508 A1 | 10/2003 | Cauthen |
| 2003/0191534 A1* | 10/2003 | Viart et al. ............... 623/17.15 |
| 2003/0199981 A1 | 10/2003 | Ferree |
| 2003/0204260 A1 | 10/2003 | Ferree |
| 2003/0204261 A1* | 10/2003 | Eisermann et al. ....... 623/17.14 |
| 2003/0208271 A1 | 11/2003 | Kuras |
| 2003/0225408 A1 | 12/2003 | Nichols et al. |
| 2003/0229358 A1 | 12/2003 | Errico et al. |
| 2003/0233097 A1 | 12/2003 | Ferree |
| 2003/0233148 A1 | 12/2003 | Ferree |
| 2004/0002759 A1 | 1/2004 | Ferree |
| 2004/0002762 A1 | 1/2004 | Hawkins |
| 2004/0024406 A1 | 2/2004 | Ralph et al. |
| 2004/0024407 A1 | 2/2004 | Ralph et al. |
| 2004/0030387 A1 | 2/2004 | Landry et al. |
| 2004/0030389 A1 | 2/2004 | Ferree |
| 2004/0030390 A1 | 2/2004 | Ferree |
| 2004/0034426 A1 | 2/2004 | Errico et al. |
| 2004/0078079 A1 | 4/2004 | Foley |
| 2006/0212123 A1* | 9/2006 | Lechmann et al. ........ 623/17.15 |
| 2007/0135919 A1* | 6/2007 | Aebi et al. ............... 623/17.11 |

* cited by examiner

ARTIFICIAL INTERVERTEBRAL DISC HAVING A UNIVERSAL JOINT

CROSS-REFERENCE TO RELATED APPLICATIONS

This application claims the benefit of the filing date of U.S. Provisional Patent Application No. 60/546,230 filed Feb. 20, 2004, the disclosure of which is hereby incorporated by reference herein.

BACKGROUND OF THE INVENTION

The bones and connective tissue of an adult human spinal column consist of more than twenty discrete bones coupled sequentially to one another by a tri-joint complex, which consists of an anterior disc and two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine up to the base of the skull, includes the first seven vertebrae. The intermediate twelve bones are the thoracic vertebrae, and connect to the lower spine comprising the five lumbar vertebrae. The base of the spine comprises the sacral bones (including the coccyx). The component bones of the cervical spine are generally smaller than those of the thoracic spine, which are in turn smaller than those of the lumbar region. The sacral region connects laterally to the pelvis.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification. Referring now to FIGS. 6a and 6b, in which a side perspective view of an intervertebral body cage and an anterior perspective view of a post implantation spinal column are shown, respectively, a more complete description of these devices of the prior art is herein provided. These cages 101 generally comprise tubular metal body 102 having an external surface threading 103. They are inserted transverse to the axis of the spine 104, into preformed cylindrical holes at the junction of adjacent vertebral bodies (in FIG. 6b the pair of cages 101 are inserted between the fifth lumbar vertebra (L5) and the top of the sacrum (S1)). Two cages 101 are generally inserted side by side with the external surface threading 103 tapping into the lower surface of the vertebral bone above (L5), and the upper surface of the vertebral bone (S1) below. The cages 101 include holes 105 through which the adjacent bones are to grow. Additional materials, for example autogenous bone graft materials, may be inserted into the hollow interior 106 of the cage 101 to incite or accelerate the growth of the bone into the cage. End caps (not shown) are often utilized to hold the bone graft material within the cage 101.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the present invention to provide an implant device that stabilizes the spine while still permitting normal motion.

It is further an object of the present invention to provide a device for implantation into the intervertebral space that does not promote the abnormal distribution of biomechanical stresses on the patient's spine.

It is further an object of the present invention to provide an artificial intervertebral disc that provides limited rotation of the baseplates transverse to the axis of the spine.

It is further an object of the present invention to provide an artificial disc that provides limited angular rotation of the baseplates relative to a centroid of motion centrally located within the intervertebral space.

It is further an object of the present invention to provide an artificial intervertebral disc that supports compression loads.

It is further an object of the present invention to provide an artificial intervertebral disc that permits the baseplates to axially float toward and away from each other.

It is further an object of the invention to provide an artificial intervertebral disc that supports tension loads.

It is further an object of the present invention to provide an artificial intervertebral disc that prevents lateral translation of the baseplates relative to one another.

It is further an object of the present invention to provide an artificial intervertebral disc that provides a centroid of motion centrally located within the intervertebral space.

It is further an object of the present invention to provide artificial intervertebral disc baseplates having outwardly facing surfaces that conform to the concave surface of adjacent vertebral bodies.

Other objects of the present invention not explicitly stated will be set forth and will be more clearly understood in conjunction with the descriptions of the preferred embodiments disclosed hereafter.

SUMMARY OF THE INVENTION

The proceeding objects are achieved by the present invention, which is an artificial intervertebral disc or intervertebral spacer device having a pair of support members (e.g., spaced-apart baseplates), each with an outwardly-facing surface. Because the artificial disc of the present invention is to be positioned between the facing endplates of adjacent vertebral bodies, the baseplates are arranged in a substantially parallel planer alignment (or slightly offset relative to one another in accordance with proper lordotic angulation) with the outwardly-facing surfaces facing away from one another. The baseplates are to mate with the vertebral bodies so as not to rotate relative thereto, but rather to permit the spinal segments to bend (in some embodiments, actually compress) relative to one another in manners that mimic the natural motion of the spinal segment. This natural motion is permitted by the performance of a ball-and-socket-type joint using a spherical member disposed between the secured baseplates, and the securing of the baseplates to the vertebral bone may be achieved through the use of a vertebral body contact element attached to the outwardly-facing surface of each baseplate.

Preferably, vertebral body contact elements include, but are not limited to, one or more of the following: a convex mesh, a convex solid dome and one or more spikes, as disclosed in U.S. patent application Ser. No. 10/256,160, the disclosure of which is hereby incorporated by reference herein.

The ball and socket joint of the present invention permit rotation between the two elements by capturing a strap integrally formed with one of the baseplates within a groove of the other baseplate. The strap, preferably, has an inner surface having a curvature which is substantially equal to the curvature of a ball also disposed between the two baseplates, thereby permitting rotation and angulation of the strap about a central point of the ball. This further permits angulational movement and rotational movement of one baseplate relative to the other baseplate.

The groove of the other baseplate, i.e., second baseplate, has a wider dimension than the strap so as to permit the strap to move freely about the central point of the ball at least with a desired angulation and rotation range. Additionally, the groove has a depth, which, in conjunction with the space between the first baseplate and the ball, limits the ability of the strap to come into contact with a bottom surface of the groove, even during axial movement of the two baseplates.

In one preferred embodiment, the ends of the groove are angled relative thereto so as to reduce wear and tear between the strap and groove as the strap angulates and rotates about the central point of the ball within the groove.

In one embodiment of the present invention, the artificial intervertebral disc includes a first baseplate having a top surface, a bottom surface and an aperture extending therebetween. The first baseplate further includes a strap having a top surface, a bottom surface, a first end and a second end. The ends of the strap are remote from one another and are attached to the bottom surface of the first baseplate such that a portion of the strap underlies the aperture.

The artificial intervertebral disc of the present invention also includes a second baseplate having a top surface, a bottom surface and a cavity exposed at the top surface of the second baseplate. The cavity preferably includes a groove having a first sidewall and a second sidewall, with the sidewalls being remote from each other. A spherical element having a central point is disposed within the aperture of the first baseplate and overlies the strap. The spherical element is preferably attached to the first sidewall and second sidewall of the second baseplate such that the strap is positioned and captured within the groove, thereby permitting the first baseplate and the second baseplate to move in an angulational direction and a rotational direction relative to one another with the strap translating about the central point of the spherical element.

The first sidewall and second sidewall may each include an indent such that the spherical element is attached to the first sidewall and second sidewall at respective indents. Additionally, the first sidewall and second sidewall may have a plurality of ends that are angled, such that during rotational movement of the first baseplate or second baseplate the strap has an increased range of motion within the groove.

The artificial intervertebral implant of the present invention may also include a cover having a bottom surface. The cover is preferably designed to be at least partially disposed within the aperture such that the cover overlays the spherical element, thereby capturing the spherical element between the cover and strap.

In certain embodiments of the present invention, the cover may include a cap and post with the top surface of the first baseplate further including a recess circumferentially extending about the aperture such that the post of the cover is compression fit within the aperture and the cap of the cover is compression fit within the recess.

The groove of the second baseplate may have a bottom surface and the spherical element may have an apex. Additionally, a distance between the bottom surface of the groove to the apex of the spherical element is preferably greater than a distance between the bottom surface of the cover to the bottom surface of the strap. More preferably, the distance between the top surface of the strap to the bottom surface of the cover is greater than a diameter of the spherical element, such that the combination of the two permits the first baseplate and the second baseplate to move in an axial direction relative to one another.

In one preferred embodiment of the present invention, the bottom surface of the cover and top surface of the strap have a radius of curvature substantially equal to a radius of curvature of the spherical element, such that the strap and the cover pivot about the central point of the spherical element as the first baseplate moves relative to the second baseplate in both an angulational direction and a rotational direction.

In one aspect of the present invention a distance between the top surface of the strap and the bottom surface of the cover is greater than a length of the articulating element, such that the first baseplate and the second baseplate may move in an axial direction relative to one another.

The bottom surface of the cover and the top surface of the strap may have a radius of curvature substantially equal to a radius of curvature of the articulating element, such that the strap and the cover may translate about the articulating element.

In another aspect of the present invention the aperture may be partially defined by the strap and not be included within the first baseplate.

In another aspect of the present invention the articulating element may be stationary relative to a first element, with the strap being captured between the articulating element and the first element.

DETAILED DESCRIPTION

The present invention will now be described with reference to the accompanying figures. The embodiments described herein are meant to be illustrative of the present invention and in no way should be thought of as limiting the present invention.

Figure 1:
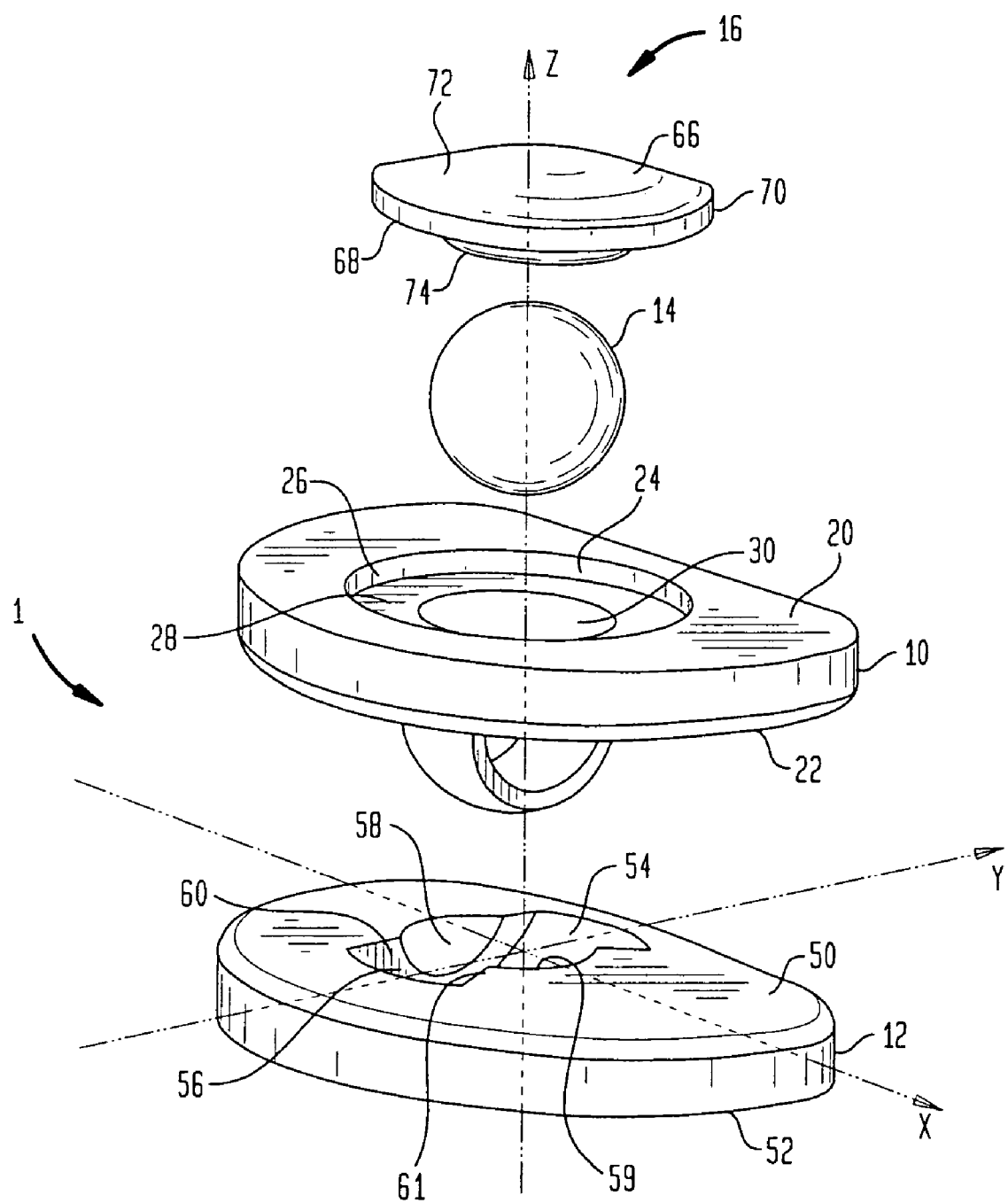
FIG. 1 illustrates a perspective exploded view of a device according to the present invention.

As shown in FIG. 1, an artificial intervertebral disc 1, according to the present invention, preferably includes an upper baseplate 10, a lower baseplate 12, a ball 14 and a cover 16. Upper baseplate 10 is provided with a top surface 20 and a bottom surface 22. Disposed within the boundary of top surface 20 is a recess 24. Recess 24 includes a circular skirt 26 positioned adjacent top surface 20 and defining the outer boundary of recess 24. Recess 24 further includes a shoulder 28 defining a lower limit of the recess. An aperture 30 is disposed adjacent shoulder 28 and extends from the shoulder to bottom surface 22 of upper baseplate 10.

Figure 2:
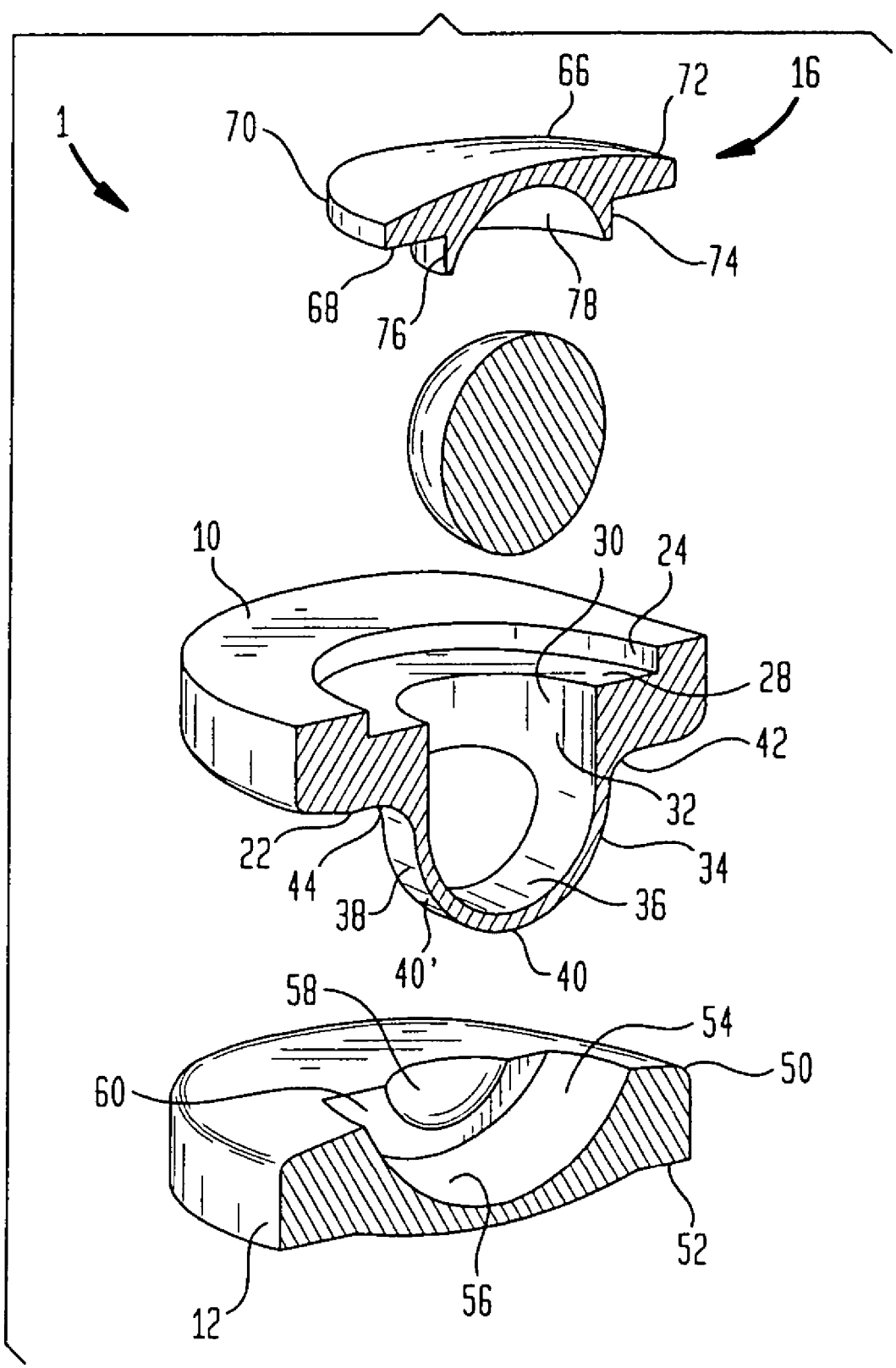
FIG. 2 illustrates an exploded cross-sectional view of the device of FIG. 1.

As best shown in FIG. 2 aperture 30 is defined by circumferential wall 32 which extends adjacent and between shoulder 28 and bottom surface 22. Also as shown in FIG. 2, upper baseplate 10 includes a strap 34. Strap 34 preferably includes a substantially semispherical inner surface 36 and a substantial semispherical outer surface 38. Inner surface 36 and outer surface 38 are attached to one another through edges 40 and 40' extending between the two surfaces and defining remote sides of strap 34. Inner surface 36 and outer surface 38 have ends remote from one another and preferably include a first chamfered end 42 and a second chamfered end 44. Chamfered ends 42, 44 extend from bottom surface 22 of upper baseplate 10 downward toward lower baseplate 12 and connect strap 34 to upper baseplate 10. Strap 34 may be integral with upper baseplate 10. As will be described below, aperture 30 as well as semispherical inner surface 36 of strap 34 preferably have a radius which is at least slightly larger than the radius of ball 14.

As illustrated in FIGS. 1 and 2, lower baseplate 12 preferably includes a top surface 50 and a bottom surface 52. Top surface 50 preferably includes a cavity 54 exposed near a central portion of lower baseplate 12. Cavity 54 preferably includes a groove 56 and a pair of indents 58, 59 disposed on opposite sidewalls 60, 61 positioned about groove 56. Groove 56 preferably has a generally semicircular shape—when viewing from the direction X—with opposite sidewalls 60, 61 positioned adjacent to indents 58, 59, respectively, and extending in the Y direction. Groove 56 is preferably larger in size than strap 34, so that when the artificial intervertebral disc 1 is assembled and the strap is disposed within the bounds of groove 56, as will be described below, strap 34 does not touch the bottom or sidewalls 60, 61 of groove 56. Although groove 56 is shown as having a semicircular shape—viewed from the direction X—the shape of groove 56 is not essential to the present invention so long as it is large enough such that strap 34 does not touch the bottom of groove 56 when the artificial intervertebral disc 1 is assembled. For clarity of illustration, it is to be understood that, as described below, the sizing and shaping of strap 34 and groove 56 are such that when the ball 14 is secured to lower baseplate 12, the strap 34 is freely movable about ball 14 in the space between sidewalls 60, 61 of groove 56. As previously alluded to, indents 58, 59 are disposed on opposite sidewalls 60, 61 respectively and are preferably semispherical in shape to complementarily support ball 14, as will be described below.

Ball 14 is sized so as to be able to fit within aperture 30 and be supported by strap 34. In a method of assembly, ball 14 is placed into aperture 30 through recess 24 of top surface 20.

As best illustrated in FIGS. 1 and 2, cover 16 preferably includes a top surface 66 and a bottom surface 68. Cover 16 further includes a circumferential edge 70 extending between top surface 66 and bottom surface 68. Top surface 66, bottom surface 68 and edge 70 define a cap portion 72 of cover 16. Cover 16 further includes a cylindrical post 74 having a circumferential skirt 76 adjacent to and extending down from bottom surface 68. Post 74 preferably further includes a concave bottom surface 78, the concavity of which may extend into cap portion 72 of cover 16. The radius of curvature of concave bottom surface 78 (best shown in FIG. 2) is preferably configured to approximate the curvature of ball 14. In a preferred embodiment, cylindrical post 74 has a diameter that is slightly smaller than the diameter of aperture 30 extending through upper baseplate 10.

In a method of assembly, ball 14 is placed within aperture 30 so as to be supported by strap 34 of upper baseplate 10. Subsequently, cover 16 is placed within recess 24 of upper baseplate 10 with cylindrical post 74 preferably being compression-fit or locked within aperture 30. Additionally, in a preferred embodiment cap portion 72 may also be compression fit to upper baseplate 10 by edge 70 of cover 16 being engaged with skirt 26 of the upper baseplate.

Figure 4A:
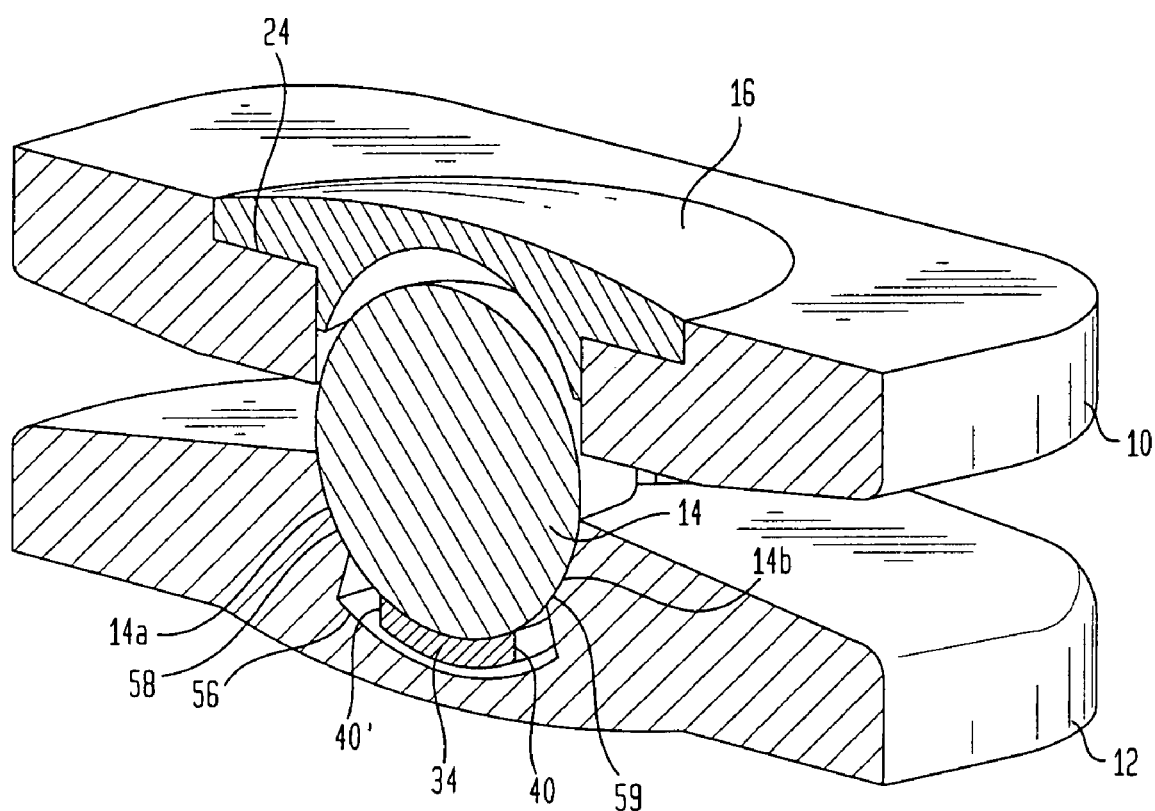
FIG. 4A illustrates an assembled perspective cross-sectional view of the device of FIG. 1 taken along the Y axis.
Figure 4B:
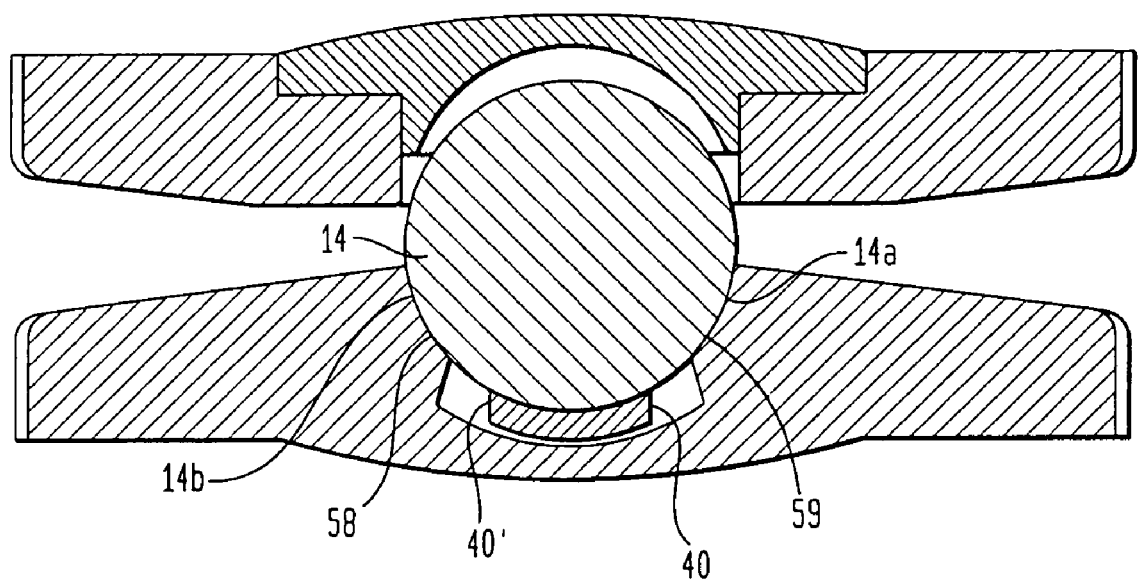
FIG. 4B illustrates an assembled cross-sectional view of the device of FIG. 1 taken along the Y axis.

As best shown in FIGS. 4A and 4B, strap 34 preferably has a width extending from edge 40 to edge 40' that is smaller than the width of groove 56 defined by sidewalls 60 and 61. This configuration allows strap 34 and upper baseplate 10 to rotate around a central point of ball 14 about an axis parallel to axis Z (FIG. 1) (angulational and rotational motion). Such a relative rotation in the transverse plane is limited to some extent by the limited space between sidewalls 60 and 61 of groove 56 and edges 40 and 40' of strap 34.

Figure 5:
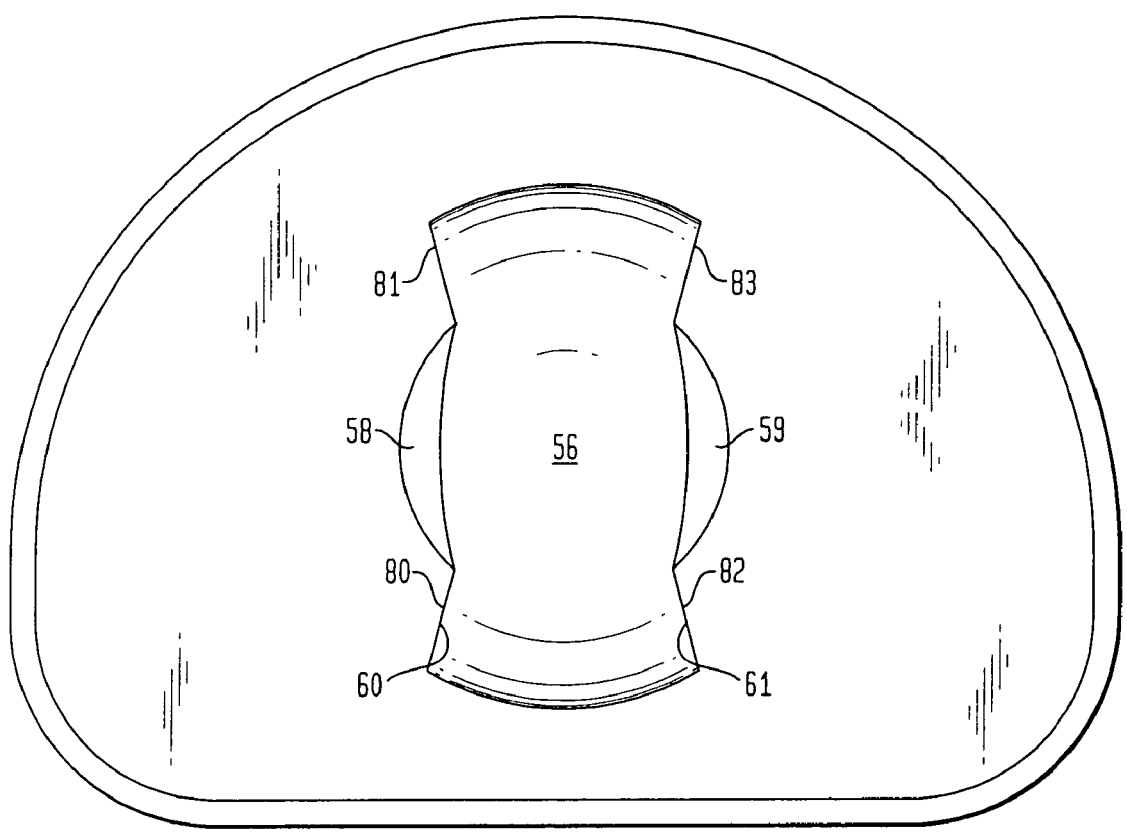
FIG. 5 illustrates a top view of a lower baseplate used in the present invention.
Figure 6A:
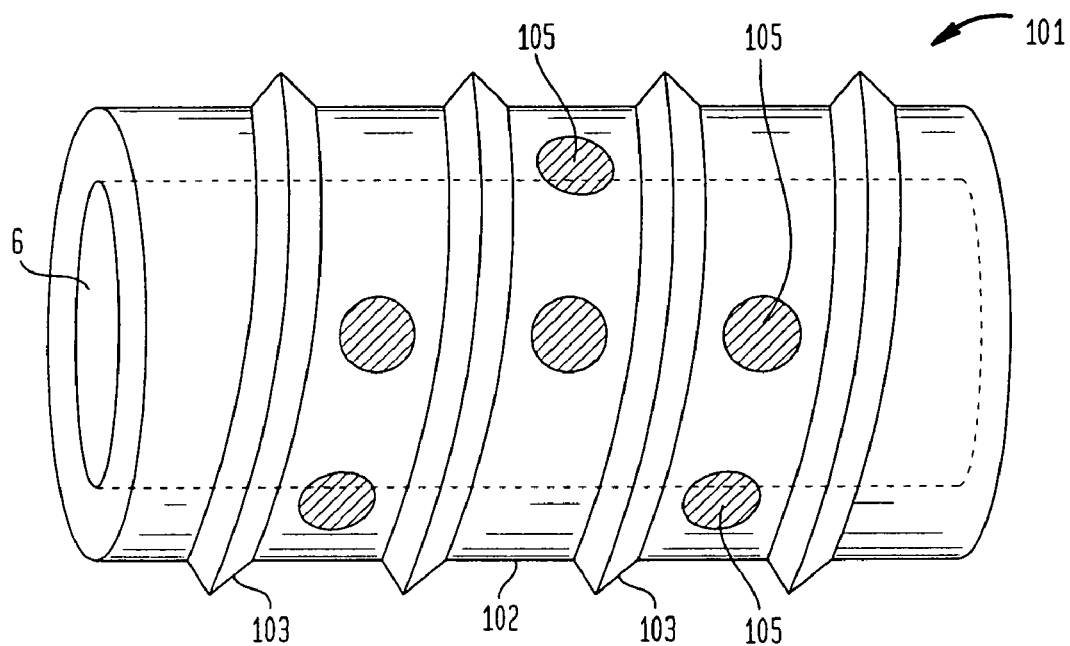
FIG. 6A illustrates a prior art embodiments of an artificial intervertebral disc.
Figure 6B:
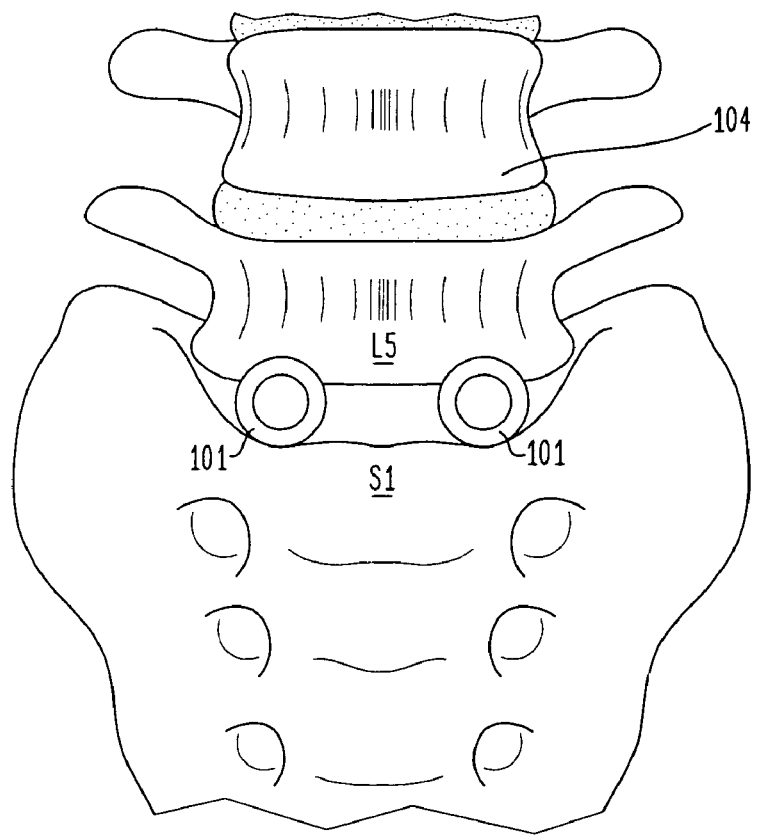
FIG. 6B illustrates prior art embodiments of an artificial intervertebral disc.

In one preferred embodiment, as shown in FIG. 5, sidewalls 60 and 61 of groove 56 are angled at their respective ends 80, 81, 82, and 83 relative to one another to accommodate desired rotation and angulation ranges and/or limit rotation to within a desired range of angles, without inviting excess wear or line contact endured by edges 40 and 40' of strap 34 against sidewalls 60 and 61. That is, if sidewalls 60 and 61 were not angled, the edges 40 and 40' will dig into the sidewalls, causing undesirable wear characteristics over multiple articulations of the device; whereas if the sidewalls 60 and 61 are angled to align with the edges 40 and 40' of strap 34 during the maximum desired axial rotation range, edges 40 and 40' will hit flush against sidewalls 60 and 61, minimizing wear debris and improving the wear characteristics of the device.

Rotation (or articulation) of upper baseplate 10 about an axis perpendicular to axis Z, (lateral bending articulation and flexion-extension articulations) relative to lower baseplate 20 can be limited by the distance between bottom surface 22 of upper baseplate 10 and top surface 50 of lower baseplate 12. In other words, such articulation will be stopped when the two surfaces 22 and 50 come to meet each other. This distance can be determined by properly designing the size of ball 14 as well as the position (depth) of indents 58 and 59 on sidewalls 60 and 61, respectively in lower baseplate 20 and the dimensions of groove 56 in the lower baseplate, which will be further described below.

Figure 3:
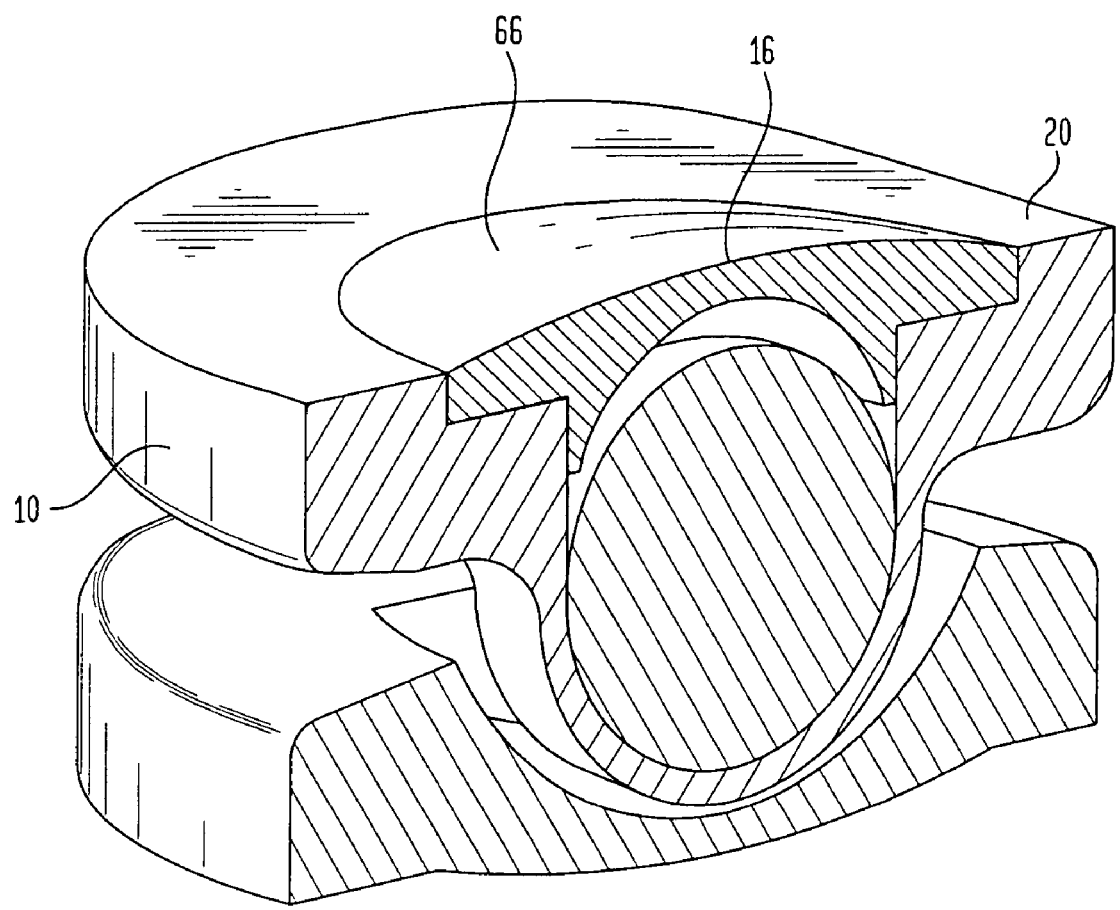
FIG. 3 illustrates an assembled cross-sectional view of a device of FIG. 1 taken along the Y axis.

Top surface 20 of upper baseplate 10 and bottom surface 52 of lower baseplate 20 are preferably designed to be convex in shape to match the concave shape of endplates of adjoining vertebral bones. Similarly, the top surface 66 of cover 16 preferably has a convex design and is a smooth extension of top surface 20 of upper baseplate 10 as best shown in FIGS. 1 and 3.

To assemble the artificial intervertebral disc 1 of the present invention, as previously mentioned, ball 14 is placed through recess 24 of upper baseplate 10 and into aperture 30 so as to be supported by strap 34. With ball 14 resting on semispherical inner surface 36 of strap 34, the strap is placed within groove 56 of lower baseplate 12, with portions 14A, and 14B of ball 14, contacting respective indents 58 and 59 as best illustrated in FIGS. 4A and 4B. Portions 14A and 14B of ball 14 are then fixed to respective indents 58 and 59 by, for example, welding or an adhesive, whereby the ball is fixed to lower baseplate 12, and strap 34 is retained in groove 56 by ball 14. This also prevents upper baseplate 10 from disengaging from lower baseplate 12. Cover 16 is next disposed within recess 24 of upper baseplate 10. Preferably, cover 16 is secured to upper baseplate 10 by a compression lock, threading, an adhesive or the like.

After the assembling is finished, artificial intervertebral disc 1 can be implanted between the adjoining endplates of vertebral bones. Strap 34 and therefore upper baseplate 10, can articulate and rotate about a center of ball 14 in universal directions relative to lower baseplate 12. The distance between upper baseplate 10 and lower baseplate 12 limits the articulation about an axis perpendicular to axis Z. Moreover, upper baseplate 10 can move toward and away from (along axis Z) lower baseplate 12 with such a translation being limited by the space between cover 16 and ball 14 as well as the distance between ball 14 and the bottom surface of groove 56. Angulational and rotation (rotation about an axis perpendicular to the axis Z) are limited by the difference between the width of strap 34 and the width of groove 56 and, preferably, opposing walls 60 and 61 of groove 56 being angled relative to one another to accommodate desired motion ranges, and/or limit motion to within a desired range of angles, without inviting excess wear or line contact of the edges 40 and 40' against the sidewalls 60 and 61.

Alternatively, although not shown in the drawings, edges 40 and 40' of strap 34 and/or sidewalls 60 and 61 of groove 56 are not necessarily flat, but can be curved (concave/convex) in shape, which may result in a smoother contact between the strap and the groove.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An artificial intervertebral disc comprising:
   a first baseplate having a top surface, a bottom surface, an aperture extending from said top surface through to said bottom surface and a strap attached to said bottom surface of said first baseplate and underlying said aperture;
   a second baseplate juxtaposed with said first baseplate, said second baseplate having a top surface, a bottom surface and a cavity exposed at said top surface of said second baseplate;
   an articulating element disposed within said aperture and overlaying said strap, said articulating element being engagable with a pair of opposing sidewalls of said second baseplate and said strap within said cavity for permitting said first and second baseplates to angulate and rotate relative to one another with said strap translating over said articulating element.

2. The artificial intervertebral implant according to claim 1, wherein said pair of opposing sidewalls include a first sidewall having a first indent and a second sidewall having a second indent, said articulating element being engagable with said first sidewall and said second sidewall at said first indent and said second indent, respectively.

3. The artificial intervertebral implant according to claim 2, wherein said pair of opposing sidewalls have a plurality of ends that are angled, such that during rotational movement of said first baseplate or said second baseplate said strap has an increased range of motion within said cavity of said second baseplate.

4. The artificial intervertebral implant according to claim 1, wherein said pair of opposing sidewalls include a plurality of ends that are angled, such that during rotational movement of said first baseplate or said second baseplate said strap has an increased range of motion within said cavity of said second baseplate.

5. The artificial intervertebral implant according to claim 1, further comprising a cover having a bottom surface, said cover being at least partially disposed within said aperture such that said cover overlies said articulating element thereby capturing said articulating element between said cover and said strap.

6. The artificial intervertebral implant according to claim 5, wherein said cover further includes a cap and a post, wherein said top surface of said first baseplate includes a recess circumferentially extending about said aperture, wherein said post of said cover is compression fit within said aperture and said cap of said cover is compression fit within said recess.

7. The artificial intervertebral implant according to claim 5, wherein said distance between said top surface of said strap and said bottom surface of said cover is greater than a length of said articulating element, such that said first baseplate and said second baseplate may move in an axial direction relative to one another.

8. The artificial intervertebral implant according to claim 7, wherein said bottom surface of said cover and said top surface of said strap have a radius of curvature substantially equal to a radius of curvature of said articulating element, such that said strap and said cover translate about said articulating element as said first baseplate moves relative to said second baseplate in both an angulational direction and a rotational direction.

9. The artificial intervertebral disc according to claim 1, wherein said articulating element is a ball.

10. The artificial intervertebral implant according to claim 1, wherein said strap is integrally formed with said first baseplate.

11. An artificial intervertebral implant comprising:
    a first baseplate having a top surface, a bottom surface and a strap having a first end and a second end, said first end and said second end of said strap being remote from one another and attached to said bottom surface of said first baseplate such that said strap underlies said first baseplate, said strap at least partially defining an aperture therethrough;
    a second baseplate juxtaposed with said first baseplate, said second baseplate having a top surface and a bottom surface;
    an articulating element disposed within said aperture at least partially defined by said strap and attached to said second baseplate; and wherein said strap attached to said first baseplate extends between said articulating element and said second baseplate and wherein said strap is free to rotate and angulate about said articulating element within a desired range of angles.

12. The artificial intervertebral implant according to claim 11, wherein said strap is continuous.

13. The artificial intervertebral implant according to claim 11, wherein said aperture extends from said strap to said top surface of said first baseplate.

14. The artificial intervertebral implant according to claim 11, wherein said top surface of said second baseplate includes a cavity having a pair of opposing sidewalls, said articulating element attached to said second baseplate at said pair of opposing sidewall, said strap being retained at least partially underlying said articulating element and disposed within said cavity of said second baseplate such that said strap is free to translate about said articulating element within a desired range of angles.

* * * * *